United States Patent [19]

Cloutier et al.

[11] Patent Number: 5,725,580
[45] Date of Patent: Mar. 10, 1998

[54] HOLE CAPS FOR PROSTHETIC IMPLANTS

[75] Inventors: Raymond J. Cloutier, Gainesville; Cary M. Mauldin, Lake City, both of Fla.

[73] Assignee: Exactech, Inc., Gainesville, Fla.

[21] Appl. No.: 680,276

[22] Filed: Jul. 11, 1996

Related U.S. Application Data

[63] Continuation of Ser. No. 357,855, Dec. 16, 1994, abandoned.

[51] Int. Cl.$^6$ .................................................. A61F 2/28
[52] U.S. Cl. ............................................................ 623/16
[58] Field of Search .................................... 623/16, 18, 22, 623/23; 292/256.63

[56] References Cited

U.S. PATENT DOCUMENTS

| | | | |
|---|---|---|---|
| 1,765,239 | 6/1930 | Meurling | 292/256.63 |
| 2,401,856 | 6/1946 | Brock | 411/517 |
| 3,023,925 | 3/1962 | Sher | 220/307 |
| 4,320,421 | 3/1982 | Larson et al. | 360/60 |
| 4,536,897 | 8/1985 | Powell | 623/6 |
| 4,566,138 | 1/1986 | Lewis et al. | |
| 4,795,468 | 1/1989 | Hodorek | 623/18 |
| 4,919,666 | 4/1990 | Buchhorn et al. | 623/16 |
| 4,955,325 | 9/1990 | Zarnowski et al. | 623/22 |
| 4,973,844 | 11/1990 | O'Farrell et al. | 250/341 |
| 5,226,917 | 7/1993 | Schryver | 623/22 |
| 5,435,455 | 7/1995 | Prüss | 220/307 |

FOREIGN PATENT DOCUMENTS

| | | | |
|---|---|---|---|
| 434/604 A1 | 6/1991 | European Pat. Off. | |
| 2651996 | 3/1991 | France | 623/22 |
| 9103994 | 4/1991 | WIPO | 623/16 |

OTHER PUBLICATIONS

Joint Medical Products, Advertisement for The ZTT Acetabular Cup–A step ahead, Arthopor Oblong Cups for Acetabular Defects.

*Primary Examiner*—David H. Willse
*Attorney, Agent, or Firm*—Fish & Richardson P.C.

[57] ABSTRACT

An apparatus and method of use directed towards protective and supportive hole caps for prosthetic implant devices are disclosed. The present hole cap supports a prosthesis and provides a physical barrier between the prosthesis and underlying bone matter. In a preferred embodiment, the hole cap includes at least one compression spring formed along the perimeter of the cap. The compression spring maintains the hole cap within a counter-bored hole after the hole cap is inserted within the counter-bored hole. In accordance with the present invention, the compression spring deflects slightly towards the center of the hole cap when the cap is inserted within the counter-bored hole. The compression spring provides sufficient compression force against the sidewalls of the counter-bored hole to thereby hold the hole cap in place within the hole. The counter-bored hole is preferably shaped to snugly receive the outer perimeter of the hole cap. Alternative configurations are disclosed for maintaining the hole cap within an associated hole formed in the implant. The hole caps are used for covering holes in implants affixed to a patient's body with or without the use of bone screws. The hole caps prevent the flow of unwanted debris into the counter-bored hole and into the patient's underlying bone matter.

9 Claims, 11 Drawing Sheets

FIG. 1

PRIOR ART

HOLE CAPS FOR PROSTHETIC IMPLANTS

This is a continuation of application Ser. No. 08/357,855, filed Dec. 16, 1994, now abandoned.

BACKGROUND OF THE INVENTION

1. Field of the Invention

This invention relates generally to prosthetic implants, and more particularly to such implants which use caps or covers to support the prosthesis and to maintain a physical barrier between the prosthesis and the bone to which the prosthesis is secured.

2. Description of Related Art

Figure 1:
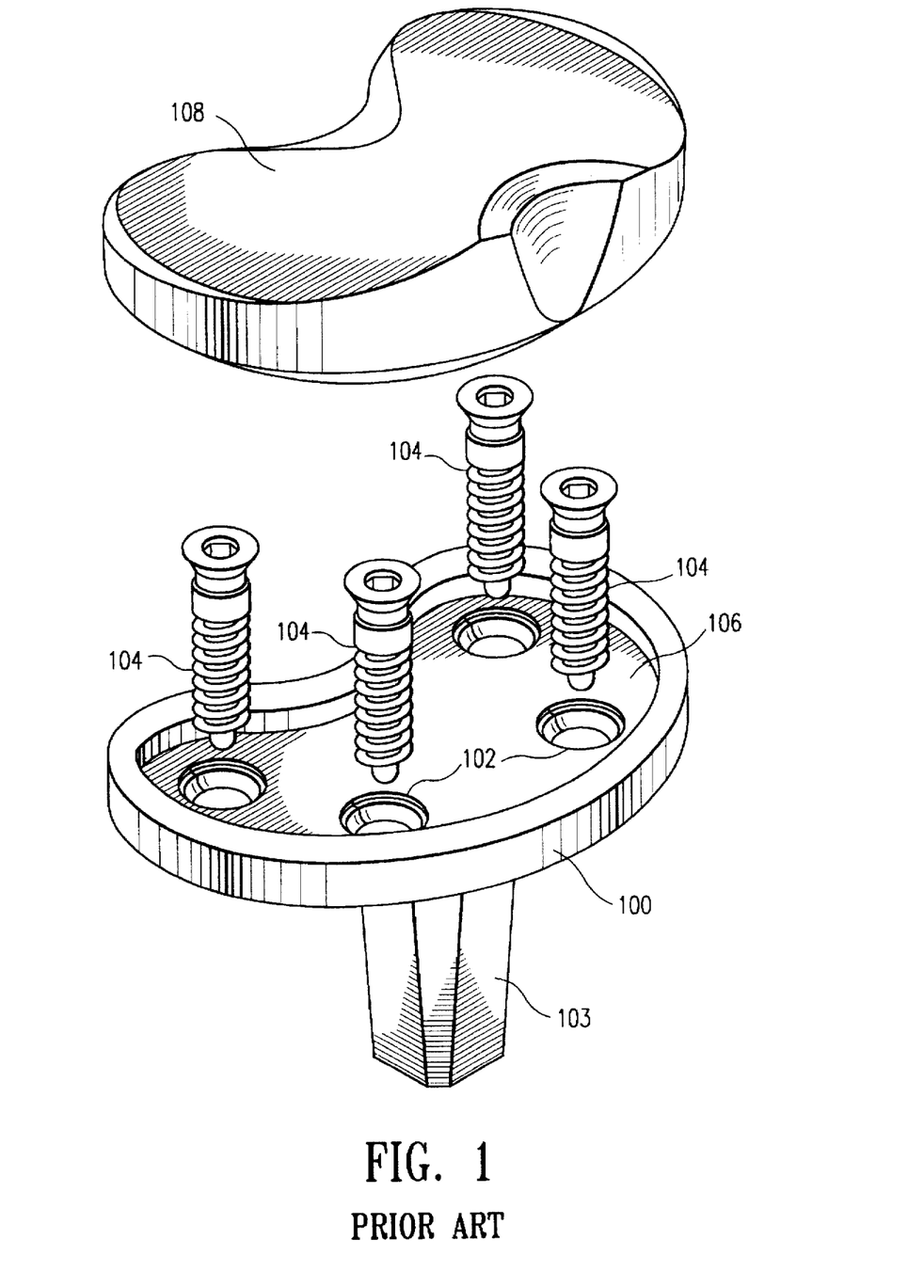
FIG. 1 is a front perspective exploded view of a tibial tray insert including a plurality of screw holes designed to receive a plurality of bone screws.

Prosthetic implant devices for replacement of damaged or deteriorating portions of bone are well known in the art. There are currently two prevailing means used to secure prosthetic implants to the patient's bone: bone cement or a plurality of bone fixation screws. Both bone cement and fixation screws can be used separately or together to ensure that the implant is secured to the patient's bone. Many commercially available prosthetic implants accommodate both affixation methods. For example, as shown in FIG. 1, a tibial tray 100 includes a plurality of holes 102 which are designed to receive a plurality of bone screws 104. In practice, a surgeon prepares a patient's bone by first cleaning and then placing bone cement into a properly prepared proximal end of the tibia. The bone cement is preferably applied using a syringe or with digital pressure to obtain intrusion of bone cement into the trabeculae of the patient's tibia. The surgeon typically inserts the stem 103 of the tibial tray 100 into the prepared tibia by hand or by using an impactor or similar tool. After inserting the tibial tray 100 into the prepared tibia, the tibial cement is allowed to harden. The surgeon maintains pressure across the tibial tray 100 while the cement hardens. Supplemental fixation of the tibial tray can also be achieved by screwing the plurality of bone screws 104 into the patient's tibial bone through the plurality of holes 102 in the tibial tray 100 with or without cement. Not all holes 102 are necessarily used to receive a bone screw 104.

Disadvantageously, the plurality of bone screw holes 102 in the tibial tray 100 provide passageways for debris to pass from a top surface 106 of the tibial tray through the tibial tray 100. If a hole 102 is not occupied by a bone screw 104, and if bone cement is not used, such debris has a higher likelihood of coming into contact with the patient's underlying bone than it does if the hole 102 is occupied by a bone screw 104. As is known, unwanted debris or particles of polyethylene or metal may be generated by the articulation of the mating femoral component during use. In addition, this unwanted debris can comprise polyethylene particles, or "shavings", or metal debris which result when a polyethylene tibial insert 108 bears, over a period of time, upon the top surface 106 of the tibial tray 100. Additionally, experience has shown that the polyethylene tibial insert 108 deforms slightly when bearing the weight of a patient over a period of time, causing the polyethylene material on the bottom surface of the insert 108 to "cold flow" or protrude slightly into the holes 102 and may also lead to particle wear with time. The unwanted debris has been shown to elicit an osteolytic response in the patient's bone tissue. Disadvantageously, this response can lead to bone resorption and eventual loss of foundation strength within the patient's bone which supports the fixation of the implant 100. Eventually, the implant 100 can become loose causing further complications.

In addition, even when bone screws 104 are inserted in the holes 102, cold flow of the polyethylene tibial insert 108 into the space above the screws can cause problems. As the polyethylene material flows into the holes 102, the thickness of the polyethylene tibial insert 108 is reduced or its shape distorted, increasing the likelihood of premature wear of the prosthetic implant, and thereby reducing the bearing capability of the insert 108.

Therefore, there is a need for a mechanism which will eliminate the problems associated with the presence of bone screw holes 102 used in existing prosthetic devices. The present invention provides such a mechanism.

SUMMARY OF THE INVENTION

An inventive hole cap and associated counter-bored hole for use in protecting and supporting a prosthetic implant are disclosed. The hole cap is preferably sufficiently thick to adequately withstand loading forces produced by a prosthetic insert during use. During surgery, after inserting bone screws into a patient's body, a surgeon quickly and easily inserts the hole cap into an associated counter-bored hole to prevent the flow of unwanted debris into the counter-bored hole and thereafter into the patient's bone underlying the implant. Alteratively, the present hole cap can be used to cover bone screw holes in applications where bone screws are not used and where only bone cement is used to affix the implant to the patient's bone.

In accordance with one preferred embodiment, the present hole cap includes at least one compression spring. When deflected inwardly toward the center of the hole cap, the compression spring is designed to provide a bias force in an outward direction away from the center of the hole cap. When inserted within the counter-bored hole, the compression spring is deflected by the sidewalls of the counter-bored hole and thereby is compressed outwardly against the surface walls of the hole. During use, the outward compression force of the spring is sufficient to hold the cap in place within the counter-bored hole. The cap thereby provides a block or seal against unwanted flow of metal or plastic debris through the hole and into the patient's bone matter. The cap is easily removed by forcing an instrument through the underside of the hole in an upward direction against the cap.

In the preferred embodiment, the cap includes a flat-topped disk having a plurality of compression springs formed along the circumference of the disk. The compression springs are formed around the circumference of the cap by forming a plurality of compression spring slots along an inner diameter of the cap. Each compression spring preferably includes a protrusion formed along the tips of the springs. The protrusions are designed to ease the insertion of the caps into the counter-bored hole. The edges or corners of the disk are preferably rounded during manufacture to also ease the insertion and removal of the caps into and out of the counter-bored holes. Once inserted within the hole, the top-facing surface of the cap is substantially flush with the top surface of the implant. The configuration of the present hole cap and counter-bored hole facilitates the intrusion of bone cement into the counter-bored hole which advantageously increases the strength of the mechanical interlock between the implant and the cement mantle. The cap is preferably manufactured using an Electro-Discharge Machining (EDM) manufacturing process.

Alternative configurations for the inventive hole cap are disclosed. These alternative embodiments contemplate the use of various cap retaining means and associated implant holes which are shaped to receive the alternative cap embodiments.

The details of the preferred embodiment and the alternative embodiments of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 4 shows a detailed top view of one compression spring of the hole cap of FIG. 3a.

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

Overview

Figure 2:
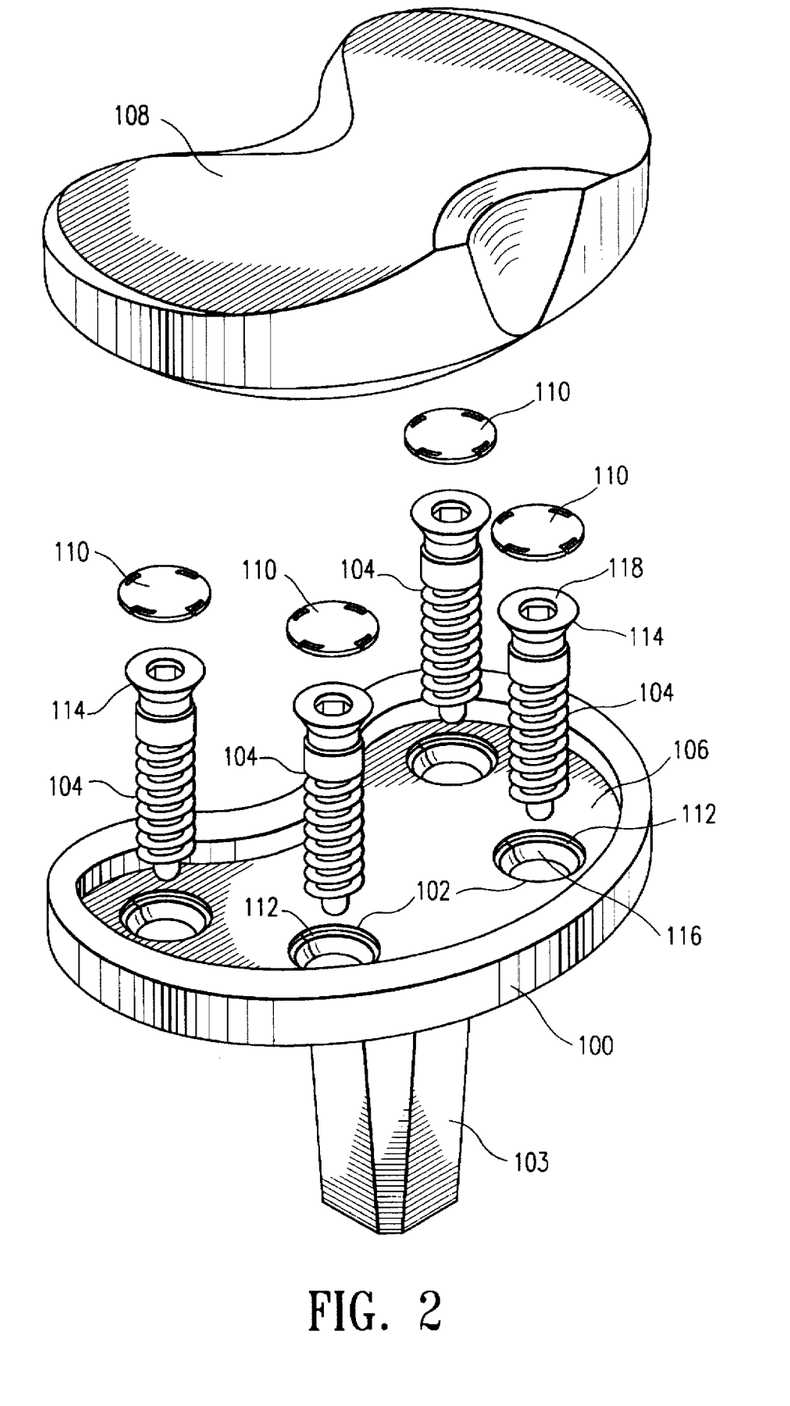
FIG. 2 is a front perspective exploded view of a tibial tray showing the hole caps and associated counter-bored holes of the present invention.

FIG. 2 shows hole caps or covers 110 and associated counter-bored holes 112 of the present invention. The invention is illustrated throughout the specification as being used in a tibial tray 100 and tibial insert prosthetic device. However, the tibial tray 100 and tibial insert 108 is exemplary only, and should not be taken as a limitation of the present invention. For example, the inventive cap 110 and counter-bored holes 112 can be used with any prosthetic device having holes for the supplemental fixation of the prosthetic device using bone screws. In particular, the present invention may be used with many other prosthetic devices including an acetabular cup, a glenoid component, an ulnar component, a vertebral body, and a bone plate.

Referring again to FIG. 2, once the tibial tray 100 is inserted within the patient's bone, the bone screws 104 can be used to affix the tray 100 to the patient's bone. The bone screws 104 may be used with or without bone cement. Once the screws are fully inserted within the holes 102, the head of the screws 114 are received by spherical screw head counter-bores 116 formed into the holes 102. When fully inserted within the holes 102, a top surface 118 in the bone screw head 114 is positioned below the top surface 106 of the tibial tray 100. With the tibial tray 100 securely attached to the bone, and the bone screws 104 fully inserted within the patient's bone, the surgeon prepares the tibial tray for the tibial insert 108 by placing the caps 110 within the counter-bored holes 112 formed in the holes 102. As shown in FIG. 2 and described in more detail hereinbelow with respect to FIGS. 5, 8 and 9, the diameter of the cap 110 and its associated counter-bored hole 112 slightly exceeds the diameter of the screw head spherical counter-bore 116. In addition, the cap 110 is manufactured sufficiently thin to provide adequate clearance between the bottom-facing surface of the cap 110 and the top surface 118 of the screw head 114. However, the cap 110 is manufactured sufficiently thick to adequately withstand loading forces produced by the insert 108 on the cap 110.

As described in more detail hereinbelow with reference to FIGS. 5 and 6, a surgeon simply inserts the cap 110 into its associated counter-bored hole 112 after the screws 104 are fully inserted within the patient's bone. The caps 110 include at least one compression spring 120, each of which compress outwardly against the surface walls of the counter-bored holes 112. During insertion, the downward force created by the surgeon's placement of a cap 110 into a counter-bored hole 112 causes each spring 120 to deflect in an inward direction toward the center of the cap 110. Once the caps 110 are fully inserted within the holes 112, the compression springs 120 compress outwardly against the surface walls of the counter-bored holes 112. The compression force of each spring 120 holds the caps 110 in place during use. While inserted within the counter-bored holes 112, the upwardly facing surface of the caps 110 are preferably flush with the top surface 106 of the tibial tray 100. Thus, the caps 110, in combination with the top surface 106 of the tibial tray, provide a substantially continuous surface against which the tibial insert 108 bears during use.

The caps 110 provide a block or a seal which prevents metal and plastic debris from flowing through the holes 102 and becoming lodged within the patient's bone. The caps 110 also provide a bearing support to the polyethylene liner or insert which prevents cold flow of polyethylene material which consequently can compromise the strength of the implant 108. The caps 110 are easily pressed into place by the surgeon by simply placing the cap 110 over the hole 102 and pressing the cap within the counter-bored hole 112. The caps 110 are easily removed from a tibial tray 100 (prior to insertion in a patient) by forcing an instrument having a smaller diameter than the diameter of the hole 102 through the underside of the hole 102 in an upward direction against the cap 110. The instrument is pressed against the underside of the caps 110 with a force that exceeds the compression force produced by the compression springs 120. The compression force exerted by the compression springs 120 is preferably approximately between 0.5 and 1.0 pound-force. Thus, in the preferred embodiment, the compression force is easily overcome by the surgeon and the caps 110 are thereby easily removed.

Details of Cap Configuration

Figure 3A:
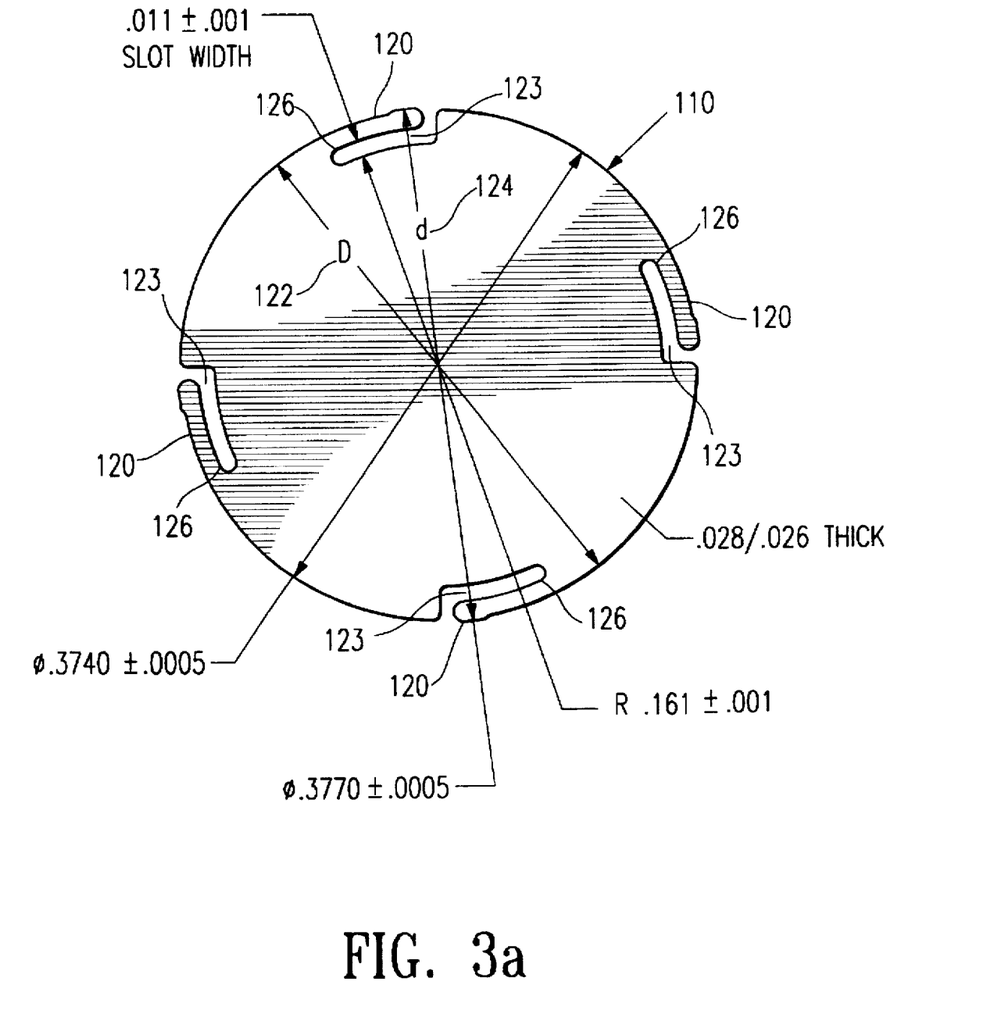
FIG. 3a shows a top plan view of the preferred embodiment of the hole cap of the present invention.

FIG. 3a shows a top view of the cap 110 of the present invention. As shown in FIG. 3a, and described above, each cap 110 preferably comprises a flat-topped disk having at least one compression spring 120 formed along the perimeter of the cap 110. The diameter "D" 122 of the cap 110 is manufactured to be slightly smaller than the diameter of the counter-bored hole 112 (FIG. 2) into which the cap 110 is inserted during use. The difference in diameters between the diameter D 122 and the diameter of the hole 112 preferably ranges between −0.0005 to 0.0025 inches. The caps 110 are manufactured so that the diameter d 124 is always greater than the diameter D 122. This ensures that the sidewalls of the counter-bored holes 112 first contact the compression springs 120 when the cap 110 is first inserted within the holes 102. The maximum ratio of D/d is preferably approximately 0.995. The ratio of the diameter d 124 over the diameter of the counter-bore hole 112 ranges between approximately 1.009 (max) to 1.001 (min).

As shown in FIG. 3a, the preferred cap 110 includes a plurality of compression springs 120 formed along its circumference. Although FIG. 3a shows the cap 110 having four compression springs 120, one or more compression springs may be used. The compression springs 120 are formed around the circumference of the cap 110 by forming a plurality of compression spring slots 126 as shown in FIG. 3a. The slots 126 provide an area into which the compression springs 120 are deflected when the cap 110 is fully inserted within the counter-bored hole 112 of the tibial tray 100 (FIG. 2). Although the preferred embodiment of the hole cap is shown in FIG. 3a, a number of alternative embodiments are contemplated. For example, alternative embodiments of the inventive hole caps 110 having alternative configurations are shown in FIGS. 3b–3g.

Figure 3B:
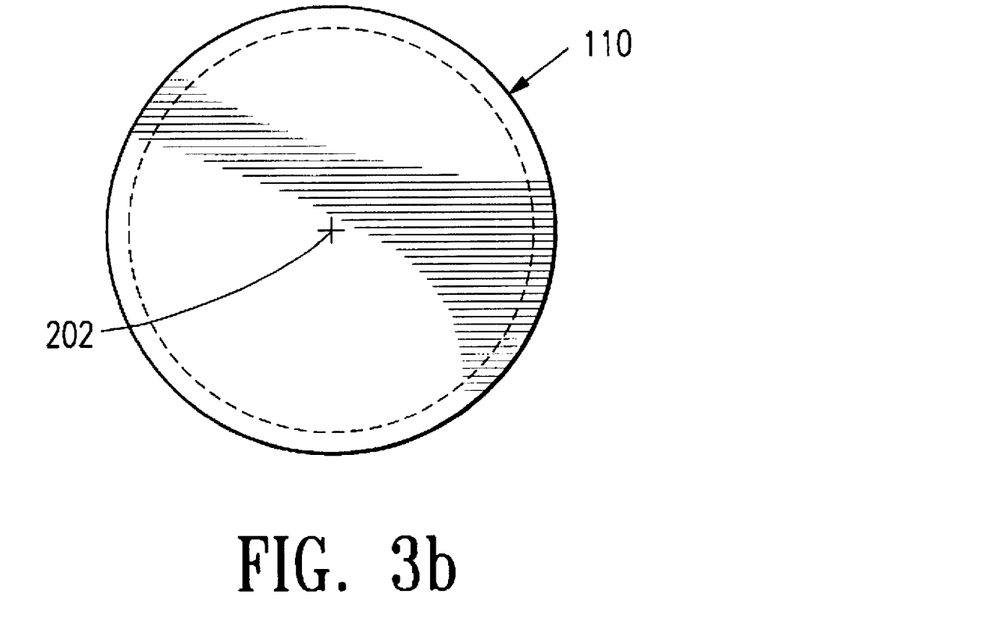
FIG. 3b shows a top plan view of a first alternative embodiment of the inventive hole cap.
Figure 3C:
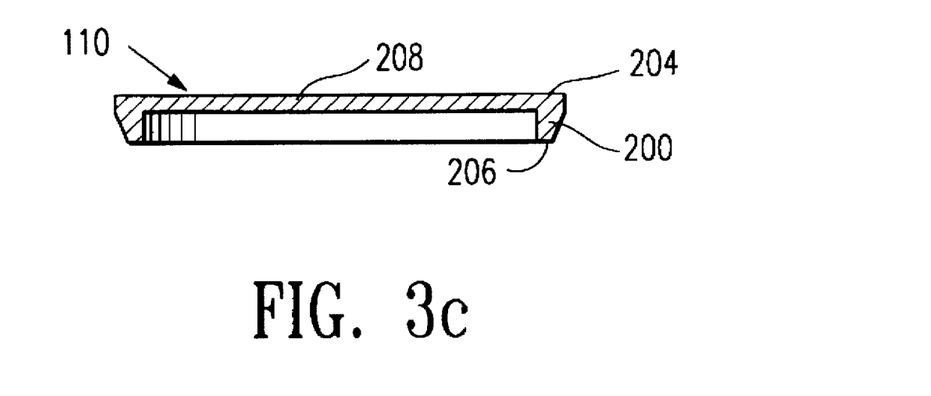
FIG. 3c shows a side cross-sectional view of the hole cap shown in FIG. 3b.

FIG. 3b shows a top plan view of a first alternative embodiment of the hole cap 110 of the present invention. FIG. 3c shows a side cross-sectional view of the hole cap 110 shown in FIG. 3b. Now referring simultaneously to both FIGS. 3b and 3c, the hole cap 110 includes sidewalls 200 which are formed to fit within the counter-bored hole 112 shown in FIG. 2. As shown in FIG. 3c, the sidewalls 200 are preferably inclined slightly toward a center 202 of the cap 110 starting from a top-facing surface 204 down toward a bottom-facing surface 206. By forming the sidewalls 200 in the manner shown in FIG. 3c, the hole caps 110 have a slightly greater diameter at its top-facing surface 204 than it does at its bottom-facing surface 206.

The diameter of the cap 110 at its bottom-facing surface 206 is preferably slightly less than the diameter of the counter-bored hole 112 (FIG. 2) into which the cap 110 is to inserted during use. When a surgeon inserts the cap 110 shown in FIGS. 3b and 3c into a counter-bored hole, a top plate 208 of the cap 110 bows slightly in an upward direction so that the top-facing surface 204 of the cap 110 is slightly convex. The dimensions of the hole cap 110 and the hole 112 are designed so that the top plate is not permanently deformed by the bowing action beyond the elastic range of either the cap 110 or the hole 112. That is, the top plate is not deformed beyond its yield strength.

When the cap 110 is fully inserted within an associated counter-bored hole 112, the bowing action of the top plate 208 causes the sidewalls 200 to exert a compression force against the sidewalls of the hole 112 in a direction away from the center 202 of the cap 110. This force is preferably within the elastic range of both the counter-bored hole material and the cap 110. Thus, the force exerted by the cap 110 shown in FIGS. 3b and 3c does not permanently deform the sidewalls of the counter-bored hole 112.

Figure 3D:
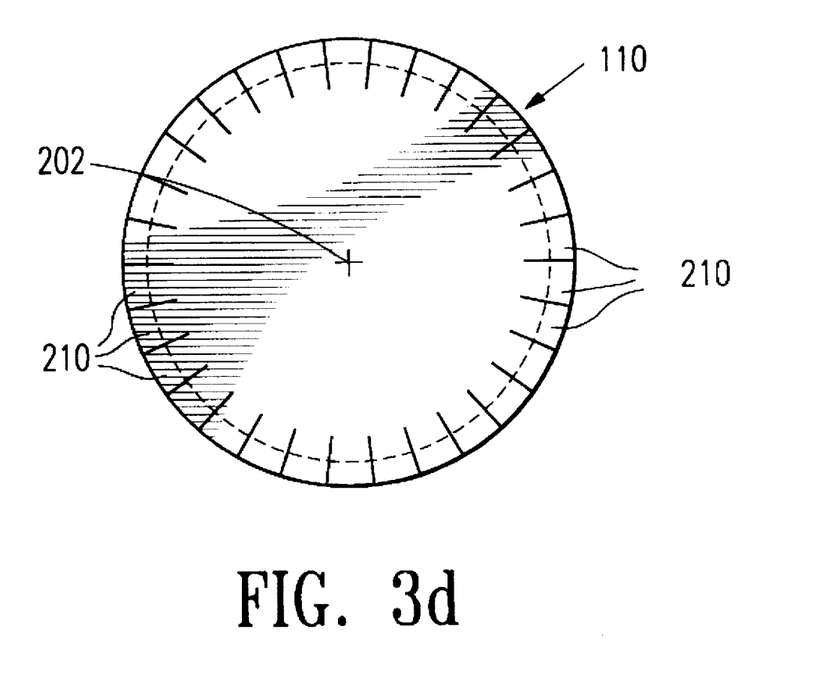
FIG. 3d shows a top plan view of a second alternative embodiment of the inventive hole cap.
Figure 3E:
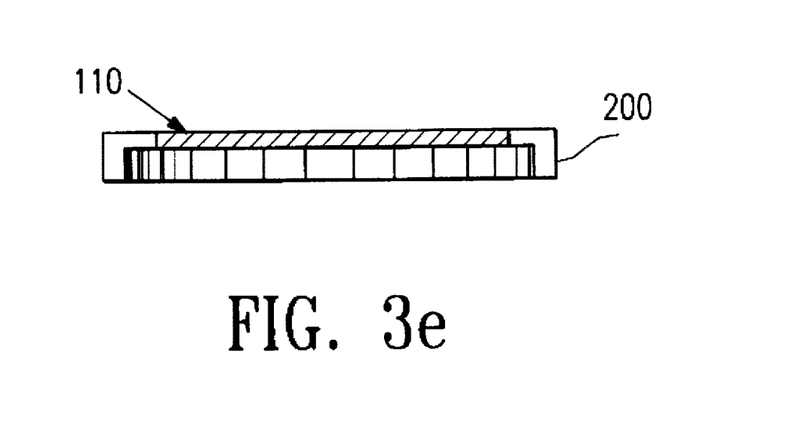
FIG. 3e shows a side cross-sectional view of the hole cap shown in FIG. 3d.

FIGS. 3d and 3e show a second alternative embodiment of the hole cap 110 of the present invention. FIG. 3d shows a top plan view and FIG. 3e shows a side cross-sectional view of the second alternative embodiment of the hole cap 110. Referring simultaneously to both FIGS. 3d and 3e, the hole cap 110 includes a plurality of inwardly facing flexible "teeth" 210 formed along the perimeter of the cap. Unlike the first alternative embodiment of FIGS. 3b and 3c, the sidewalls 200 of the cap 110 are not inclined. Rather, the sidewalls 200 are shaped so that the cap 110 has a slightly greater diameter than the diameter of the counter-bored hole 112 into which the cap is inserted during use.

When the cap 110 is inserted within its associated counter-bored hole, compression forces are exerted upon the sidewalls 200 in a direction toward the center 202 of the cap 110. Due to their flexible construction, the teeth 210 flex in an inward direction. The maximum compression forces exerted upon the teeth 210 are preferably below the yield strength of the teeth 210.

Consequently, the teeth 210 do not permanently deform after multiple insertions. Because the teeth 210 are attached to an inner portion of the cap 110, when the cap is inserted within the hole 112, the teeth 210 are biased to exert a force in an outward direction away from the center 202 of the cap 110. This outward force is sufficient to maintain the cap 110 within the hole 112 during use.

Figure 3F:
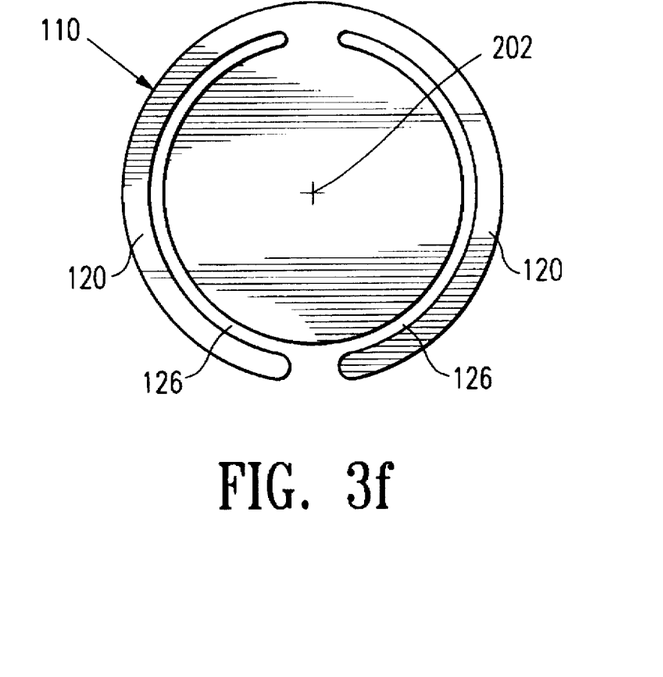
FIG. 3f shows a top plan view of a third alternative embodiment of the inventive hole cap.

FIG. 3f shows a top plan view of a third alternative embodiment of the inventive cap 110. Similar to the embodiment shown in FIG. 3a, the embodiment shown in FIG. 3f includes compression springs 120 formed along the outer circumference of the cap 110. The compression springs 120 are formed into the cap 110 by forming a plurality of compression spring slots 126 into the cap as shown in FIG. 3f. The slots 126 and springs 120 shown in FIG. 3f are elongated relative to those shown in FIG. 3a. As described above with reference to the preferred embodiment shown in FIG. 3a, the compression springs 120 flex in an inward direction when inserted within an associated counter-bored hole. The springs 120 exert a sufficient force away from the center 202 of the cap 110 and against the sidewalls of the hole 112 to prevent the cap from inadvertently disengaging from the hole 112 during use.

Figure 3G:
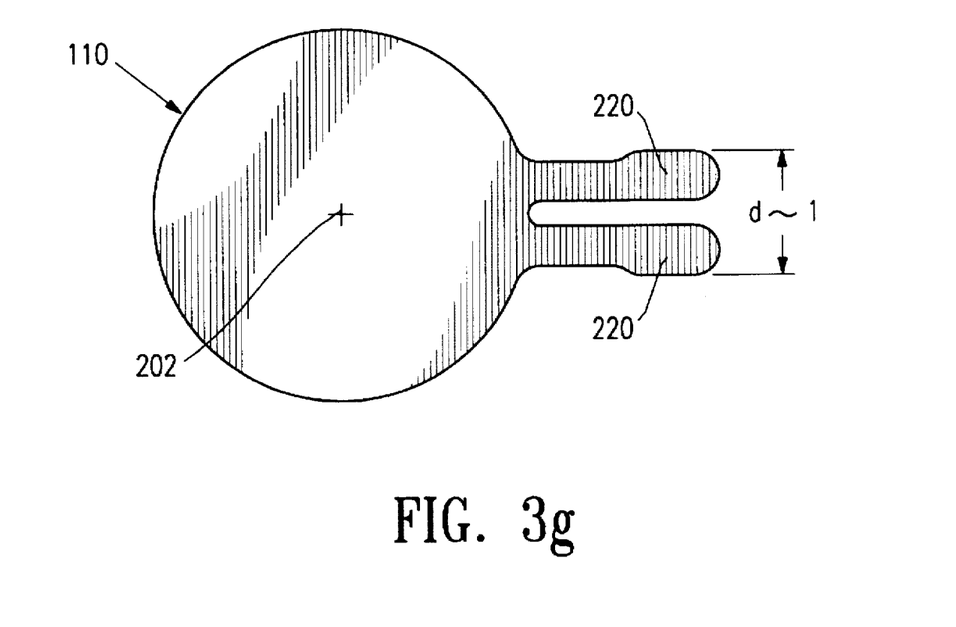
FIG. 3g shows a top plan view of a fourth alternative embodiment of the inventive hole cap.

FIG. 3g shows a top plan view of a fourth alternative embodiment of the hole cap 110 of the present invention. The alternative embodiment shown in FIG. 3g differs from those shown in FIGS. 3a–3f in that it includes at least two substantially parallel mating tines 220 which extend away from the center 202 of the cap 110. The mating tines 220 may be manufactured as an integral part of the cap 110 or may optionally be attached to the rounded cap after the cap is manufactured. The tines 220 are preferably positioned proximate each other as shown in FIG. 3g.

Although not shown, the fourth alternative embodiment shown in FIG. 3g is intended to be used with a prosthetic device which includes an insertion slot shaped to receive the cap 110 and the mating tines 220. Thus, when the cap 110 shown in FIG. 3g is inserted over a hole in the prosthetic device, the tines 220 align with an insertion slot on the prosthetic device. The distance "d" 222 between the outer edges of the mating tines 220 is preferably slightly greater than the width of the insertion slot on the prosthetic device. Therefore, when the mating tines 220 are inserted within the insertion slot, the tines 220 flex inwardly toward one another. Consequently, the tines 220 exert a compression force in a direction away from one another when fully inserted within the insertion slot on the prosthetic device. This compression force is sufficient to maintain the cap 110 in place during use.

Figure 4:
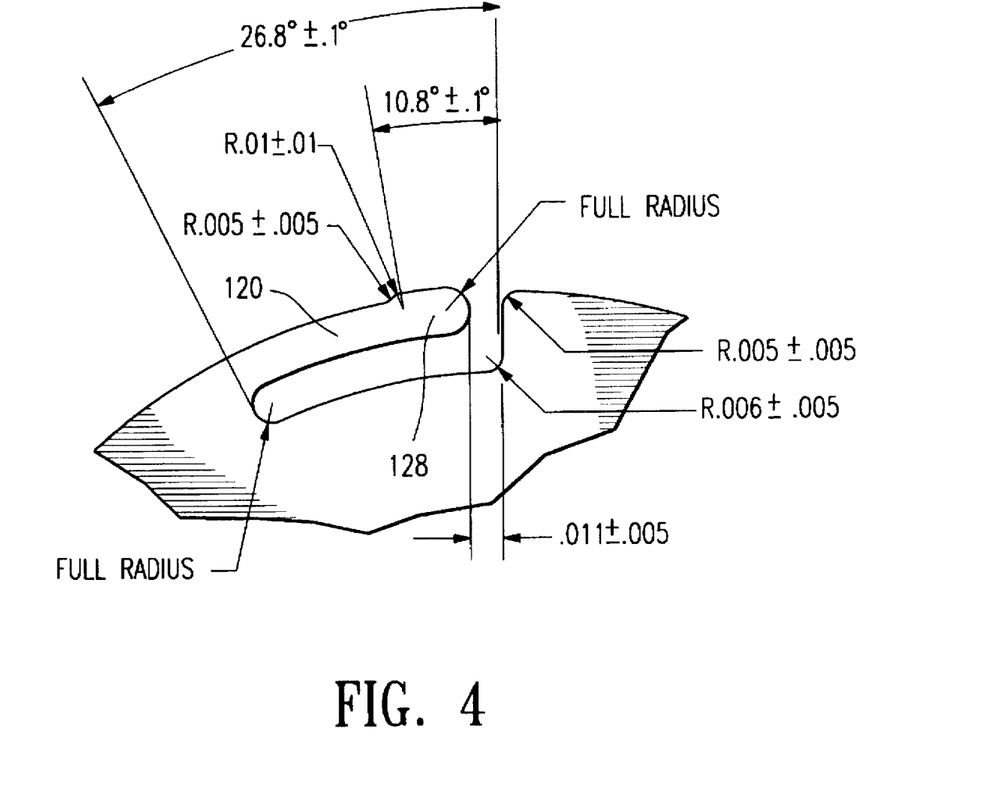

FIG. 4 shows a detailed top view of one compression spring 120 shown in FIG. 3a. The compression springs 120 preferably include a protrusion 128 formed along tips of the springs 120. As shown in FIG. 4, the diameter of the cap 110, when measured from the outer periphery of the protrusion 128, is slightly larger than the diameter of the cap 110 when measured from the outer periphery of the remainder of the spring 120. That is, the provision 128 extends a distance slightly beyond the rest of the perimeter of the hole cap 110. The distance that the protrusion 128 extends beyond the perimeter of the hole cap is preferably approximately between 0.001 to 0.010 in.

Figure 5:
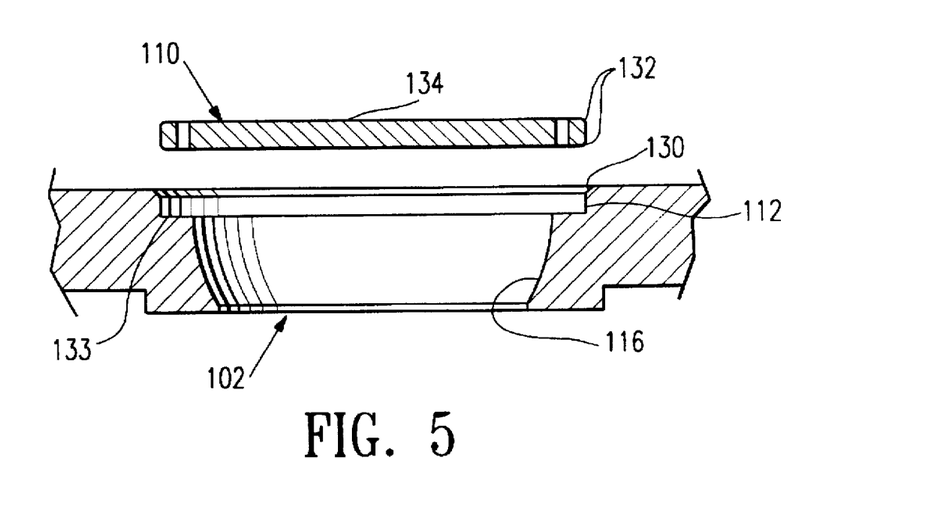
FIG. 5 shows a cross-sectional view of the screw hole and the hole cap of FIGS. 2-4.

FIG. 5 shows a cross-sectional view of the hole 102 and the inventive cap 110 of FIGS. 2–4. The bone screw hole 102 preferably includes a counter-bored hole 112 configured to receive the cap 110 when the cap 110 is inserted within the counter-bored hole 112. As shown in FIG. 5, the diameter of the cap 110 and the counter-bored hole 112 slightly exceeds the diameter of the spherical counter-bore 116. The cap protrusions 128 (FIG. 4) extend slightly beyond the diameter of the counter-bored hole 112. In one preferred embodiment, an insertion ramp or an inclined surface 130 is milled around the top-facing surface of the counter-bored hole 112 and inclined in a direction toward the center of the counter-bored hole 112 as shown in FIG. 5. The inclined surface 130 of the counter-bored hole 112 has a diameter which is slightly larger than the diameter of the counter-bored hole 112. The inclined surface 130 allows the cap 110 to be easily centered within the counter-bored hole 112 and allows the surgeon to insert the cap within the hole 112.

During manufacture, the inventive cap 110 preferably is removed of all burrs during manufacture and is tumble-polished so that all of the edges of the cap 110 have a slightly curved corner radius. For example, the corners 132 of the cap 110 shown in FIG. 5 are slightly curved so that they have no sharp edges. The curved corners 132 of the cap 110 serve to aid assembly of the cap 110 into the counter-bored hole 112. The cap 110 is preferably inserted by a surgeon into the counter-bored hole 112 by placing the cap 110 over the hole 102 and pressing the cap against the inclined surface 130 in a downward direction toward the screw hole 102. The cap 110 may be assembled having either side facing upward, and is also rotationally independent. That is, the rotation of the cap 110 within the counter-bored hole 112 is unimportant to the operation of the implant.

During insertion, the downward force applied by the surgeon upon a top-facing surface 134 of the cap 110 causes the compression springs 120 to compress and deflect in an inward direction into an area 123 defined by the slots 126 (FIG. 3a). Some slight resistance is initially exerted by the compression springs 120 because the protrusions 128 and the compression springs 120 have a slightly greater diameter than the diameter of the counter-bored hole 112. The resistance exerted by the compression springs 120 is easily overcome due to the inclined surfaces 130 and the curved corners 132 of the cap 110. Once the surgeon overcomes the resistance exerted by the compression springs 120, the cap is pushed downward into the counter-bored hole 112. Thus, the caps 110 are self-centering within the counter-bored hole 112 once the surgeon places the cap over the hole 102 as shown in FIG. 5.

Figure 6:
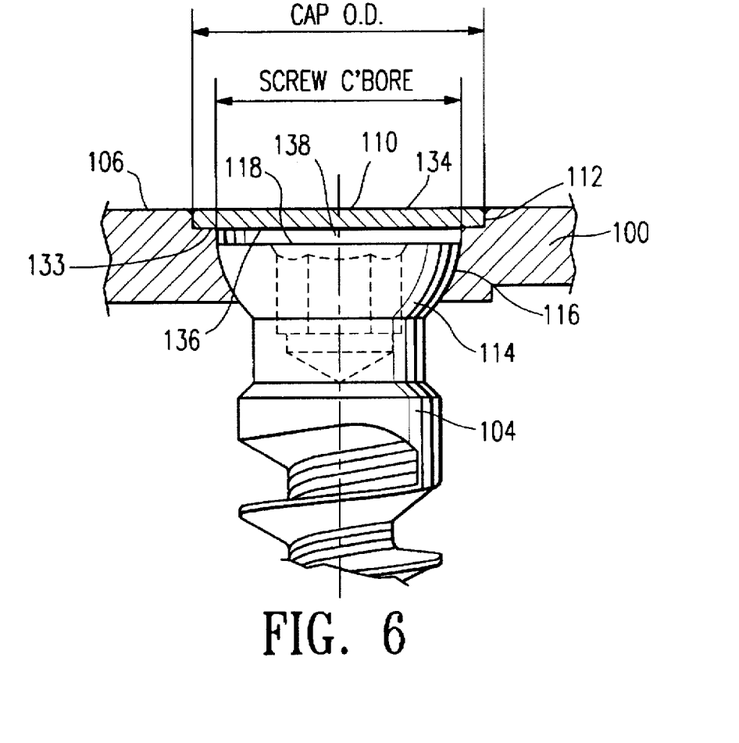
FIG. 6 shows a side cross-sectional view of the hole cap of FIGS. 2-5 showing the top-facing surface of the hole cap substantially flush with the top surface of the implant 100 after insertion of the hole cap within the counter-bored hole.
Figure 7:
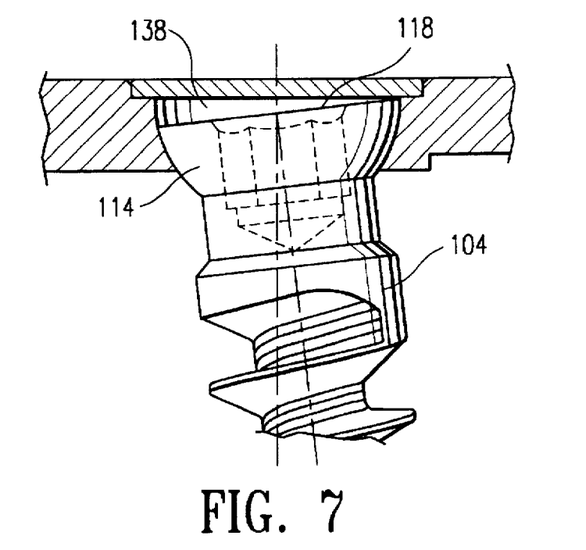
FIG. 7 shows the hole cap of FIG. 6 showing the spacing between the hole cap and the counter-bored hole which allows the bone screw head to rotate with respect to the hole cap.

Once inserted within the counter-bored hole 112, the top-facing surface 134 of the cap 110 is substantially flush with the top surface 106 of the implant 100 as shown in FIG. 6. A bottom-facing surface 136 of the cap 110 is kept a short distance away from the top surface 118 of the screw head 114 when the screw 104 is completely inserted within the patient's bone. When fully inserted within the counter-bored hole 112, the bottom surface 136 of the cap 110 and the top surface 118 of the screw head 114 define a volume 138 within which the top surface 118 of the screw head 114 can be angled or rotated. For example, as shown in FIG. 7, the spacing between the present hole cap 110 and the counter-bored hole 112 provides adequate room in the area 138 into which the bone screw head 114 can be angled or rotated. This feature is particularly advantageous because a surgeon often needs to tilt the screw 104 to reach good bone purchase.

The compression springs 120 exert a sufficient force away from the center of the cap 110 and against the sidewalls of the counter-bored hole 112 to prevent the cap 110 from inadvertently disengaging from the counter-bored hole 112 during use. The springs 120 preferably exert a compression force which falls within the elastic range of the counter-bored hole material (i.e., below the yield strength). The compression springs also preferably remain in their elastic range during insertion. That is, the force exerted by the springs 120 also falls below the yield strength of the compression springs 120. Thus, neither the springs 120, nor the sidewalls of the counter-bored hole 112, are permanently deformed during insertion and removal of the cap 110. The spring slots 126 (FIG. 3a) are designed to provide adequate room for the plurality of springs 120 to deflect into when the cap 110 is fully inserted within the counter-bored hole 112. However, the deflection area 123 formed by the slots 126 is dimensioned to be less than the width 133 of the base of the counter-bored hole 112. This ensures that unwanted debris does not pass through the slot 126 into the hole 102.

Figure 8:
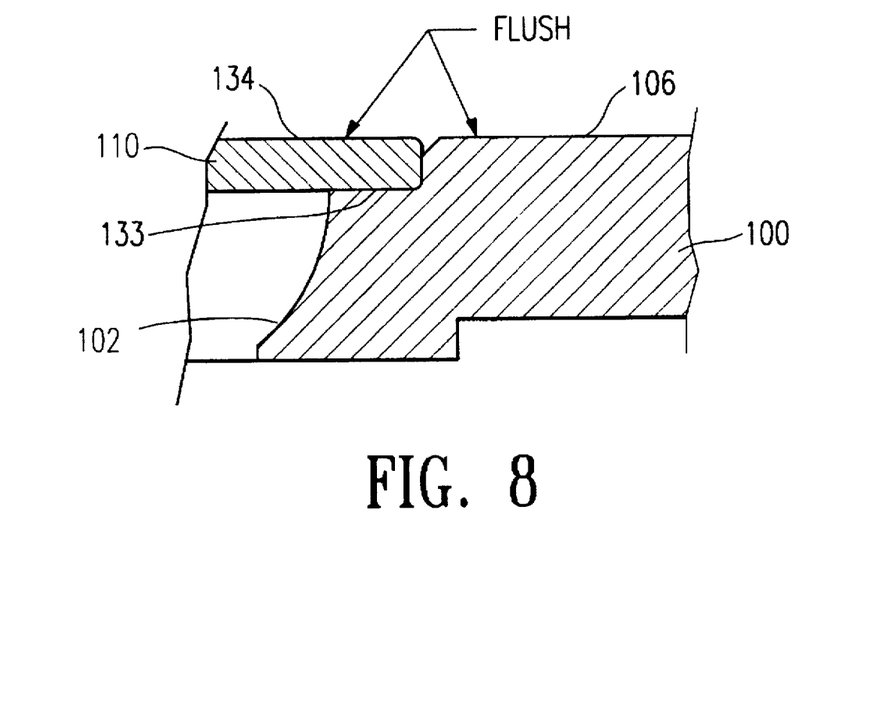
FIG. 8 shows details of the hole cap and the top surface of the implant shown in FIGS. 2-6.

FIG. 8 shows details of the cap 110 and the top surface 106 of the implant 100 shown in FIGS. 2–6. As shown in FIG. 8, when the cap 110 is fully inserted within the counter-bored hole 112, the forces exerted by the compression springs 120 (FIG. 3a) keep the cap 110 within the counter-bored hole 112. The cap provides a seal to the bone screw hole 102. When fully inserted within the counter-bored hole 112, the cap 110 prevents flow of polyethylene and metal from the top surface 106 of the insert 100 through the hole 102. The cap 110 also provides a surface upon which the insert 108 (FIG. 1) can bear during use. The cap 110 is manufactured to be relatively thin to provide adequate room for the screw head 114 and the screw head surface 118 as described above with reference to FIG. 7. However, the cap 110 must be sufficiently thick to withstand the bending loads that are applied to it via compression forces exerted by the insert 108 (FIG. 1).

Figure 9:
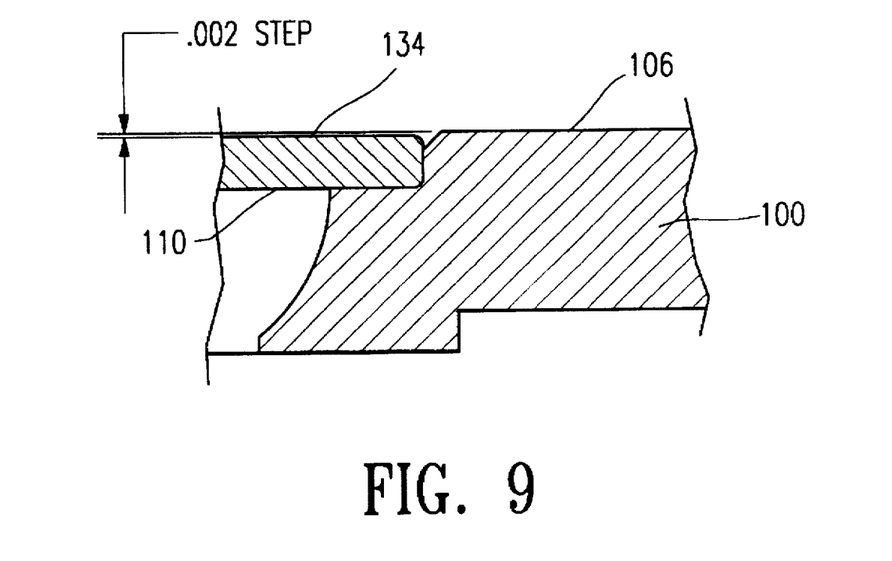
FIG. 9 shows the hole cap and counter-bored hole of FIG. 8 in their least material condition.

The thickness of the cap 110 and the depth of the counter-bored hole 112 are machined to very close tolerances. At their maximum material condition, the top-facing surface 134 of the cap 110 is exactly flush with the top surface 106 of the tray 100 as shown in FIG. 8. However, when both the cap 110 and the counter-bored hole 112 are at their least material condition, the top surface 134 of the cap 110 is not flush with the top surface 106 of the tray 100 as shown in FIG. 9. Rather, a slight step-down of preferably approximately no greater than 0.002 inches exists between the top surface 106 of the tray 100 and the top surface 134 of the cap 110. By manufacturing the cap 110 and the counter-bored hole 112 to these tolerances, the top surface 134 of the cap 110 does not interfere with the bottom-facing surface of the polyethylene insert 108 (FIG. 1). These tolerances also ensure that the cap 110 will not cause premature wear to the insert 108 nor will it interfere with the insertion of the insert 108 in the prosthetic device. The cap 110 is preferably manufactured using an Electro-Discharge Machining (EDM) manufacturing process. The caps 110 are easily and inexpensively manufactured within desired tolerances using this well-known manufacturing technique. Several caps can be concurrently machined by stacking sufficiently thin sheets of metal on top of each other. The material from which the caps are manufactured is preferably of the same type as the prosthetic implant material. For example, if the implant 100 comprises titanium alloy, the caps 100 are produced from substantially the same titanium alloy. Similarly, if cobalt chromium implants are used, the caps 110 are preferably produced from cobalt chromium. The specific materials used for the caps 110 and implants 100 are not crucial, as long as the corrosive effects of in vivo prosthetics are avoided.

Figure 10:
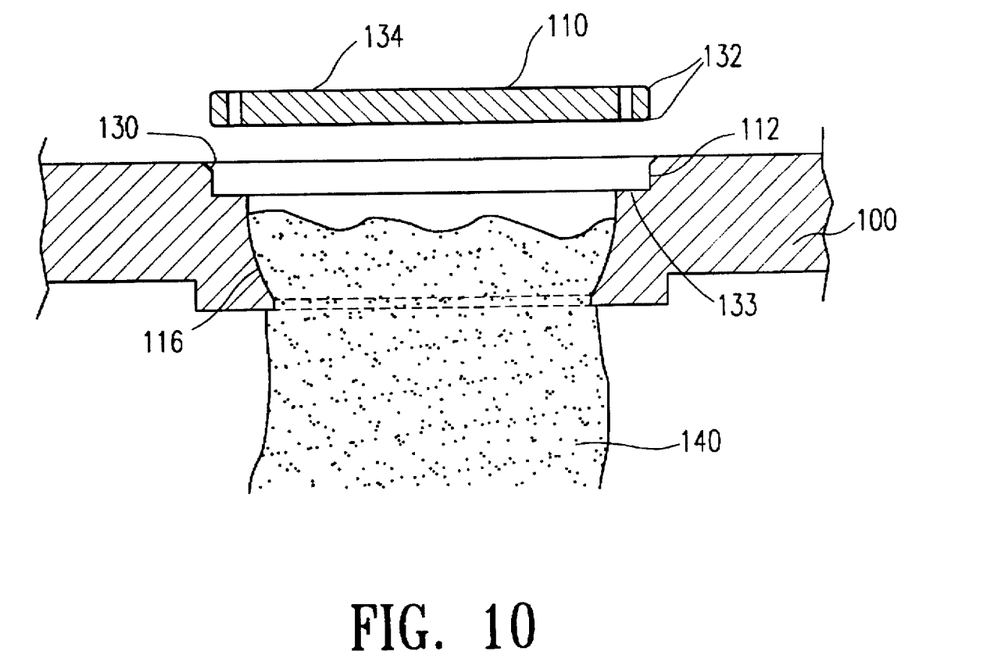
FIG. 10 shows a side cross-sectional view of the implant, hole cap, and counter-bored hole of FIG. 5, shown with the implant secured to a patient's bone using bone cement in addition to, or alternatively, in the place of the plurality of bone screws shown in FIG. 2.

FIG. 10 shows the inventive cap 110 and the counter-bored hole 112 used with an implant 100 when the implant 100 is secured to the patient's bone using bone cement 140 in addition to, or alternatively, in the place of the plurality of bone screws 104 (FIG. 2). The present invention allows bone cement to intrude into the spherical counter-bored hole 116 as shown in FIG. 10. The intrusion of bone cement 140 into the counter-bored hole 116 and the screw hole 102 creates a strong mechanical interlock between the implant and the cement mantle. Prior art prosthetic devices require a surgeon to manually prevent the intrusion of the bone cement 140 into the liner cavity. Preventing intrusion of the bone cement is a time-consuming process and thus increases operating-room time and thereby increases the costs and morbidity associated with prosthetic surgery. In addition, bone cement particles often become loose within the patient's joint, leading to foreign body abrasive wear which in turn leads to premature insert wear. As shown in FIG. 10, the present invention takes advantage of the intrusion of the bone cement 140 into the spherical counter-bored hole 116. The cap serves as a barrier to the bone cement intruding into the liner cavity.

Figure 11:
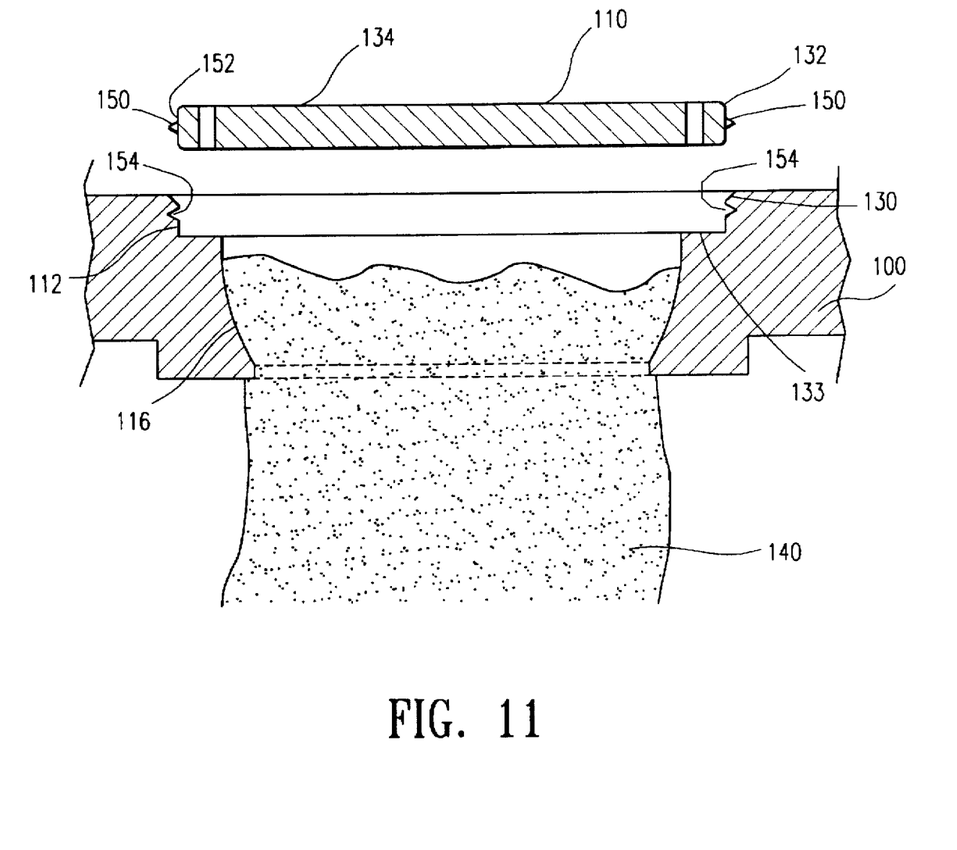
FIG. 11 shows a side cross-sectional view of an alternative embodiment of the present hole cap and counter-bored hole.

A number of embodiments of the present invention have been described. Nevertheless, it will be understood that various modifications may be made without departing from the spirit and scope of the invention. For example, FIG. 11 shows an alternative embodiment of the inventive cap 110 and the counter-bored hole 112 used with an implant 100 when the implant 100 is secured to the patient's bone. As shown in FIG. 11, the present invention contemplates an inventive cap 110 which includes a plurality of protrusions 150 formed into the sidewalls 152 of the cap 110. As shown in FIG. 11, the protrusions 150 are designed to mate with detents or undercuts 154 formed within the sidewalls of the counter-bored hole 112. Thus, when the cap 110 is inserted within the counter-bored hole 112, the protrusions 150 interlock with the detents 154 formed within the hole 112. The cap 110 is thereby secured in place within the hole 112. Accordingly, it is to be understood that the invention is not to be limited by the specific illustrated embodiment, but only by the scope of the appended claims.

We claim:

1. A hole cap for a prosthetic implant, comprising:

a. a substantially flat disk having a disk shaped inner region surrounded by an annular shaped perimeter region the disk shaped inner region having a smooth voidless surface; and b. at least one compression spring formed by a slot cut into the perimeter region of the disk, wherein the compression spring extends slightly beyond an outer diameter of the disk, but is deflected into an area defined by the slot, and wherein the cap is shaped to be received by a substantially round counter-bored hole formed into a prosthetic implant, the counter-bored hole having an inner bore and a larger outer bore such that said disk shaped inner region of the hole cap forms a substantially continuous surface along the prosthetic implant over the inner bore of the counter-bored hole and the slot cut into the perimeter region lies entirely over an area of the counter-bored hole between respective perimeters of the outer bore and inner bore, whereby debris is prevented from passing through said slots from above the disk to an area below the disk when the hole cap is inserted into the counter-bored hole.

2. The hole cap of claim 1, wherein the hole cap is substantially round.

3. The hole cap of claim 1, wherein the at least one compression spring includes a protrusion which extends the spring slightly beyond the outer diameter of the disk.

4. The hole cap of claim 1, wherein the disk comprises titanium alloy.

5. The hole cap of claim 1, wherein the disk comprises cobalt chromium alloy.

6. The hole cap of claim 1, wherein the counter-bored hole includes a cap insertion ramp, and wherein the insertion ramp has an inclined surface which assists insertion of the cap into the hole.

7. The hole cap of claim 1 wherein the diameter of the disk-shaped inner region is slightly smaller than the diameter of the annular shaped perimeter region.

8. The hole cap of claim 1 wherein a bottom outer edge of the peripheral region of the cap is rounded to facilitate insertion of the cap into the counter-bored hole.

9. The hole cap of claim 1 wherein the ratio of an external diameter of the cap at the uncompressed compression spring to a diameter of the outer bore is between 1.001 and 1.009.

* * * * *